US010208789B2

United States Patent
Maiwa et al.

(10) Patent No.: US 10,208,789 B2
(45) Date of Patent: Feb. 19, 2019

(54) DOUBLE ROW ANGULAR BALL BEARING FOR CT SCANNING DEVICE

(71) Applicant: NTN Corporation, Osaka (JP)

(72) Inventors: Tsutomu Maiwa, Mie (JP); Takahiro Kanamoto, Mie (JP); Miki Karasawa, Mie (JP)

(73) Assignee: NTN CORPORATION, Osaka (JP)

( * ) Notice: Subject to any disclaimer, the term of this patent is extended or adjusted under 35 U.S.C. 154(b) by 0 days.

(21) Appl. No.: 15/511,368

(22) PCT Filed: Sep. 9, 2015

(86) PCT No.: PCT/JP2015/075658
§ 371 (c)(1),
(2) Date: Mar. 15, 2017

(87) PCT Pub. No.: WO2016/043111
PCT Pub. Date: Mar. 24, 2016

(65) Prior Publication Data
US 2017/0254359 A1    Sep. 7, 2017

(30) Foreign Application Priority Data

Sep. 16, 2014  (JP) .................................. 2014-187296

(51) Int. Cl.
*F16C 19/18*    (2006.01)
*F16C 33/60*    (2006.01)
(Continued)

(52) U.S. Cl.
CPC ............ *F16C 19/184* (2013.01); *A61B 6/035* (2013.01); *F16C 25/06* (2013.01); *F16C 33/60* (2013.01);
(Continued)

(58) Field of Classification Search
CPC ......... F16C 19/18–19/184; F16C 33/60; F16C 2360/31; F16C 25/06; F16C 2300/14; F16C 2316/10; F16C 2240/70; A61B 6/035
See application file for complete search history.

(56) References Cited

U.S. PATENT DOCUMENTS 3,651,550 A * 3/1972 Bennett ................. F16C 19/183
29/898.09
3,652,141 A * 3/1972 Husten .................... F16C 19/30
384/455
(Continued)

FOREIGN PATENT DOCUMENTS

JP      2005-3152      1/2005
JP      2008-298117    12/2008
(Continued)

OTHER PUBLICATIONS

International Preliminary Report on Patentability and Written Opinion of the International Searching Authority dated Mar. 21, 2017 in International (PCT) Application No. PCT/JP2015/075658.
(Continued)

*Primary Examiner* — Alan B Waits
(74) *Attorney, Agent, or Firm* — Wenderoth, Lind & Ponack, L.L.P.

(57) ABSTRACT

A double-row angular contact ball bearing for a CT scanning device includes an inner member including a pair of raceway rings. The raceway rings have positioning holes into which a positioning member is inserted, to thereby suppress radial decentering of the raceway rings. Both the raceway rings are fastened by fixing bolts. The raceway rings have opposed end surfaces, and are fastened by the fixing bolts to bring the end surfaces into abutment against each other to apply a preload at a fixed position between balls and raceway surfaces. The following relationship is set: $Db/h \leq 0.26$,
(Continued)

where Db represents a diameter of each of the balls, and h represents a radial dimension from a center of each of the balls to an inner diameter of the inner member.

8 Claims, 9 Drawing Sheets

(51) Int. Cl.
    *F16C 25/06*     (2006.01)
    *A61B 6/03*     (2006.01)

(52) U.S. Cl.
    CPC ...... *F16C 2240/70* (2013.01); *F16C 2300/14* (2013.01); *F16C 2316/10* (2013.01)

(56) References Cited

U.S. PATENT DOCUMENTS

| | | | | |
|---|---|---|---|---|
| 4,730,946 A * | 3/1988 | Cain | ............... | F16C 19/187 29/445 |
| 4,746,232 A * | 5/1988 | Gugel | ............... | F16C 19/362 384/447 |
| 4,789,254 A * | 12/1988 | Marquardt | ............... | F16C 19/18 384/611 |
| 4,865,472 A * | 9/1989 | Jacob | ............... | F16C 19/184 384/503 |
| 5,639,166 A * | 6/1997 | Dittenhofer | ............... | F16C 13/02 384/454 |
| 6,367,980 B1 * | 4/2002 | Kobayashi | ............... | A61B 6/035 384/504 |
| 6,835,000 B2 * | 12/2004 | Hiramatsu | ............... | F16C 19/163 277/547 |
| 6,866,423 B2 * | 3/2005 | Faltus | ............... | F16C 23/10 384/500 |
| 7,217,038 B2 * | 5/2007 | Katou | ............... | A61B 6/035 384/445 |
| 7,435,006 B2 * | 10/2008 | Ohata | ............... | F16C 19/06 384/493 |
| 7,686,515 B2 * | 3/2010 | Schust | ............... | B62D 3/12 384/215 |
| 8,920,037 B2 * | 12/2014 | Paluncic | ............... | F16C 33/6625 384/466 |
| 9,188,161 B2 * | 11/2015 | Bouron | ............... | F16C 33/60 |
| 9,534,633 B2 * | 1/2017 | Kanamoto | ............... | F16C 19/184 |
| 9,551,324 B2 * | 1/2017 | Minadeo | ............... | F03D 1/0658 |
| 2006/0013519 A1 | 1/2006 | Fukunaga | | |
| 2015/0003986 A1 * | 1/2015 | Minadeo | ............... | F16C 33/60 416/131 |
| 2015/0056078 A1 * | 2/2015 | Pathuvoth | ............... | F03D 7/0224 416/131 |
| 2015/0192174 A1 * | 7/2015 | Shimizu | ............... | F03B 11/06 384/473 |
| 2015/0285308 A1 | 10/2015 | Kanamoto et al. | | |
| 2015/0308507 A1 * | 10/2015 | Kanamoto | ............... | F16J 15/3276 384/484 |

FOREIGN PATENT DOCUMENTS

| | | |
|---|---|---|
| JP | 2013-204678 | 10/2013 |
| JP | 2014-092231 | 5/2014 |
| WO | 2004/055399 | 7/2004 |

OTHER PUBLICATIONS

International Search Report dated Dec. 8, 2015 in International (PCT) Application No. PCT/JP2015/075658.

Extended European Search Report dated Jan. 5, 2018 in corresponding European Application No. 15841923.4.

\* cited by examiner

DOUBLE ROW ANGULAR BALL BEARING FOR CT SCANNING DEVICE

TECHNICAL FIELD

The present invention relates to a double-row angular contact ball bearing for a CT scanning device.

BACKGROUND ART

Figure 9:
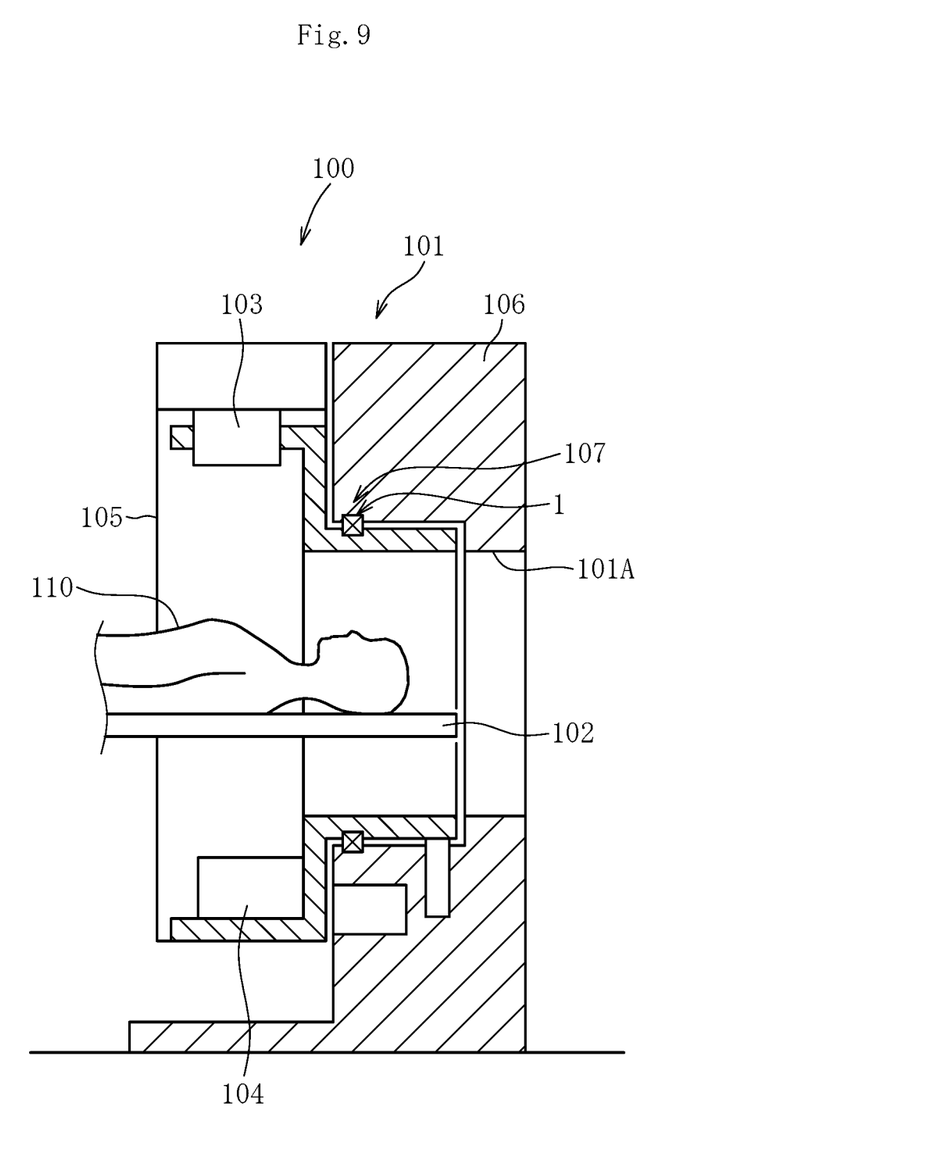
FIG. 9 is a schematic view for illustrating a CT scanning device.

In FIG. 9, an example of a CT scanning device 100 as one type of medical equipment is illustrated. The CT scanning device 100 is configured to diagnose and analyze a pathological symptom through irradiation with an X-ray or the like. The CT scanning device 100 includes an examination unit 101 having an opening 101A, and a bed unit 102 movable in the opening 101A of the examination unit 101 with an object 110 to be examined, for example, a human body, lying thereon. The examination unit 101 includes a ring-shaped rotator 105 (gantry) having an X-ray irradiation device 103 and a detection unit 104 arranged so as to be opposed to each other in a diameter direction. The rotator 105 is rotatably supported by a cylindrical stationary unit 106 through intermediation of a bearing 1.

The CT scanning device 100 is configured to rotate the rotator 105 about the bed unit 102 while irradiating the object 110 to be examined with an X-ray from the X-ray irradiation device 103 so as to detect the X-ray having passed through the object 110 to be examined with the detection unit 104, thereby obtaining a tomographic image of the object 110 to be examined.

In the CT scanning device 100, in order to form the opening 101A of the examination unit 101 into such a dimension that the object 110 to be examined may pass through the opening 101A (diameter of about 1 m), and to downsize the CT scanning device 100 itself, it is necessary to reduce a space of a rotation support unit 107 on which the bearing 1 is arranged. Therefore, a so-called ultrathin double-row angular contact ball bearing having a significantly small ball diameter with respect to a pitch circle diameter of balls is used as the bearing 1. The ultrathin double-row angular contact ball bearing refers to an ultrathin double-row angular contact ball bearing having an inner diameter of 650 mm or more and having a value of a ratio Db/PCD of a diameter Db of each of rolling elements to a pitch circle diameter PCD of the rolling elements of 0.03 or less.

In Patent Document 1, there is described a double-row angular contact ball bearing for a CT scanning device, including an inner member made up of a pair of raceway rings. Positioning holes are formed through the pair of raceway rings, and a positioning member is inserted into the positioning holes so as to suppress radial decentering of the pair of raceway rings. Both the raceway rings are fastened by a plurality of fixing bolts. The double-row angular contact ball bearing for a CT scanning device does not use a related-art spigot structure between the pair of raceway rings and suppresses the decentering of the pair of raceway rings by the positioning member inserted into the positioning holes, and is easy to manufacture and enables a cost reduction.

PRIOR ART DOCUMENTS

Patent Documents

Patent Document 1: JP 2014-92231 A

SUMMARY OF THE INVENTION

Problems to be Solved by the Invention

Bearings for a CT scanning device are required to achieve a further increase in speed and further quietness so as to alleviate anxiety of patients and prevent atrophy of internal organs. Although the double-row angular contact ball bearing for a CT scanning device described in Patent Document 1 is excellent in terms of easy manufacture and low cost, room for improvement is left for the above-mentioned requests. Attention is focused on this problem.

In view of the problem described above, the present invention has an object to provide a double-row angular contact ball bearing for a CT scanning device, which is based on a low-cost structure that is easy to manufacture with suppressed decentering achieved by inserting a positioning member through positioning holes, and is capable of achieving a further increase in speed and further quietness in the future.

Solutions to the Problems

The inventors of the present invention have conducted various examinations and verifications for a further increase in speed and further quietness based on the low-cost structure that is easy to manufacture with suppressed decentering achieved by inserting the positioning member through the positioning holes to obtain the following findings, thereby achieving the present invention.

(1) Examination of Double-Row Angular Contact Ball Bearing for CT Scanning Device in Terms of Structure In the double-row angular contact ball bearing for a CT scanning device, which has a structure in which decentering of a pair of raceway rings is suppressed by the positioning member inserted into the positioning holes (hreinafter referred to as "double-row angular contact ball bearing having a precondition structure"), the pair of raceway rings is fastened by a plurality of fixing bolts under a state in which the pair of raceway rings is centered by using a minimum necessary number of (for example, three) positioning members. It is proven that the double-row angular contact ball bearing having the precondition structure is sensitive to abnormal noise in a higher speed rotation region. The reason thereof is considered to be an effect of a fastening structure only with the fixing bolts without a spigot structure between the pair of raceway rings.

(2) Bearing Mounting Space

A mounting space for a bearing to be used is determined for each kind of CT scanning device, and therefore has a restriction that an outer-diameter dimension, an inner-diameter dimension, and a width dimension of the bearing cannot be changed. Further, a diameter of a ball as a rolling element to be incorporated into the bearing is approximately constant. As a result of various thinkings in consideration of the above-mentioned restrictions, attention is focused on a possibility of increasing a thickness of the pair of raceway rings constructing an inner member by increasing a pitch circle diameter $PCD_{BALL}$ of the ball.

(3) Verification of Limit rpm at Which Acoustic Property is Good

Under a condition where the bearing mounting space is constant, the double-row angular contact ball bearings, which each have the precondition structure with various pitch circle diameters $PCD_{BALL}$ of the ball and raceway ring thicknesses, were manufactured so as to measure a limit rpm at which an acoustic property is good (no abnormal noise is generated). As a result, it was proven that there was a difference in limit rpm at which no abnormal noise was generated even when the bearing mounting space was the same.

(4) Ideas of New Parameters

Results of the verification in the previous item were analyzed to find the following two new parameters as indices of the double-row angular contact ball bearing having the precondition structure capable of achieving a further increase in speed. As a result, the present invention was achieved.

[First Parameter]: A dimensional relationship between a diameter Db of the ball and a radial dimension h from a center of the ball to an inner diameter of the inner member.

[Second Parameter]: A dimensional relationship between a radial dimension A from a center of the fixing bolt to an outer diameter of the inner member and a radial dimension B from the center of the fixing bolt to the inner diameter of the inner member.

As a technical measure to achieve the above-mentioned object, according to a first aspect of the present invention, there is provided a double-row angular contact ball bearing for a CT scanning device, comprising:

an outer member having raceway surfaces in two rows on an inner periphery;

an inner member having raceway surfaces in two rows on an outer periphery and being arranged on an inner side of the outer member;

balls in two rows incorporated between the raceway surfaces of the outer member and the raceway surfaces of the inner member; and retainers configured to hold the balls, the inner member being made up of a pair of raceway rings, the pair of raceway rings having positioning holes into which a positioning member is inserted, to thereby suppress radial decentering of the pair of raceway rings, both the pair of raceway rings being fastened by a plurality of fixing bolts, the pair of raceway rings having opposed end surfaces that are formed as flat surfaces and being fastened by the plurality of fixing bolts to bring the opposed end surfaces into abutment against each other to apply a preload at a fixed position between the balls and the raceway surfaces, the following relationship being set:

$$Db/h \leq 0.26,$$

where Db represents a diameter of each of the balls, and h represents a radial dimension from a center of each of the balls to an inner diameter of the inner member.

Further, according to a second aspect of the present invention, there is provided a double-row angular contact ball bearing for a CT scanning device, comprising:

an outer member having raceway surfaces in two rows on an inner periphery;

an inner member having raceway surfaces in two rows on an outer periphery and being arranged on an inner side of the outer member;

balls in two rows incorporated between the raceway surfaces of the outer member and the raceway surfaces of the inner member; and retainers configured to hold the balls, the inner member being made up of a pair of raceway rings, the pair of raceway rings having positioning holes into which a positioning member is inserted, to thereby suppress radial decentering of the pair of raceway rings, both the pair of raceway rings being fastened by a plurality of fixing bolts, the pair of raceway rings having opposed end surfaces that are formed as flat surfaces and being fastened by the plurality of fixing bolts to bring the opposed end surfaces into abutment against each other to apply a preload at a fixed position between the balls and the raceway surfaces, the following relationship being set:

$$B > A,$$

where A represents a radial thickness from a center of each of the plurality of fixing bolts to an outer diameter of the inner member, and B represents a radial thickness from the center of each of the plurality of fixing bolts to an inner diameter of the inner member.

With the configuration described above, the double-row angular contact ball bearing for a CT scanning device, which is easy to manufacture to enable a cost reduction, and is capable of achieving a further increase in speed and further quietness in the future, can be realized.

Specifically, it is preferred that the double-row angular contact ball bearing have a back-to-back arrangement. As a result, a distance between working points is increased to provide higher stiffness, which is advantageous against a moment load.

It is preferred that a ratio of the diameter of each of the balls to a total bearing width be set to satisfy $Db/L \geq 0.21$, where L represents a total bearing width of the double-row angular contact ball bearing for a CT scanning device. As a result, a reduction in space can be achieved.

Through use of a reamer bolt as the above-mentioned positioning member, good workability in positioning is provided and a commercial item can be appropriately adopted. Therefore, the reamer bolt is preferred in terms of quality and cost.

Effects of the Invention

According to the present invention, it is possible to realize the double-row angular contact ball bearing for a CT scanning device, which is easy to manufacture to enable a cost reduction, and is capable of achieving a further increase in speed and further quietness in the future.

EMBODIMENTS OF THE INVENTION

A double-row angular contact ball bearing for a CT scanning device according to a first embodiment of the present invention is described with reference to FIG. 1 to FIG. 6.

Figure 1:
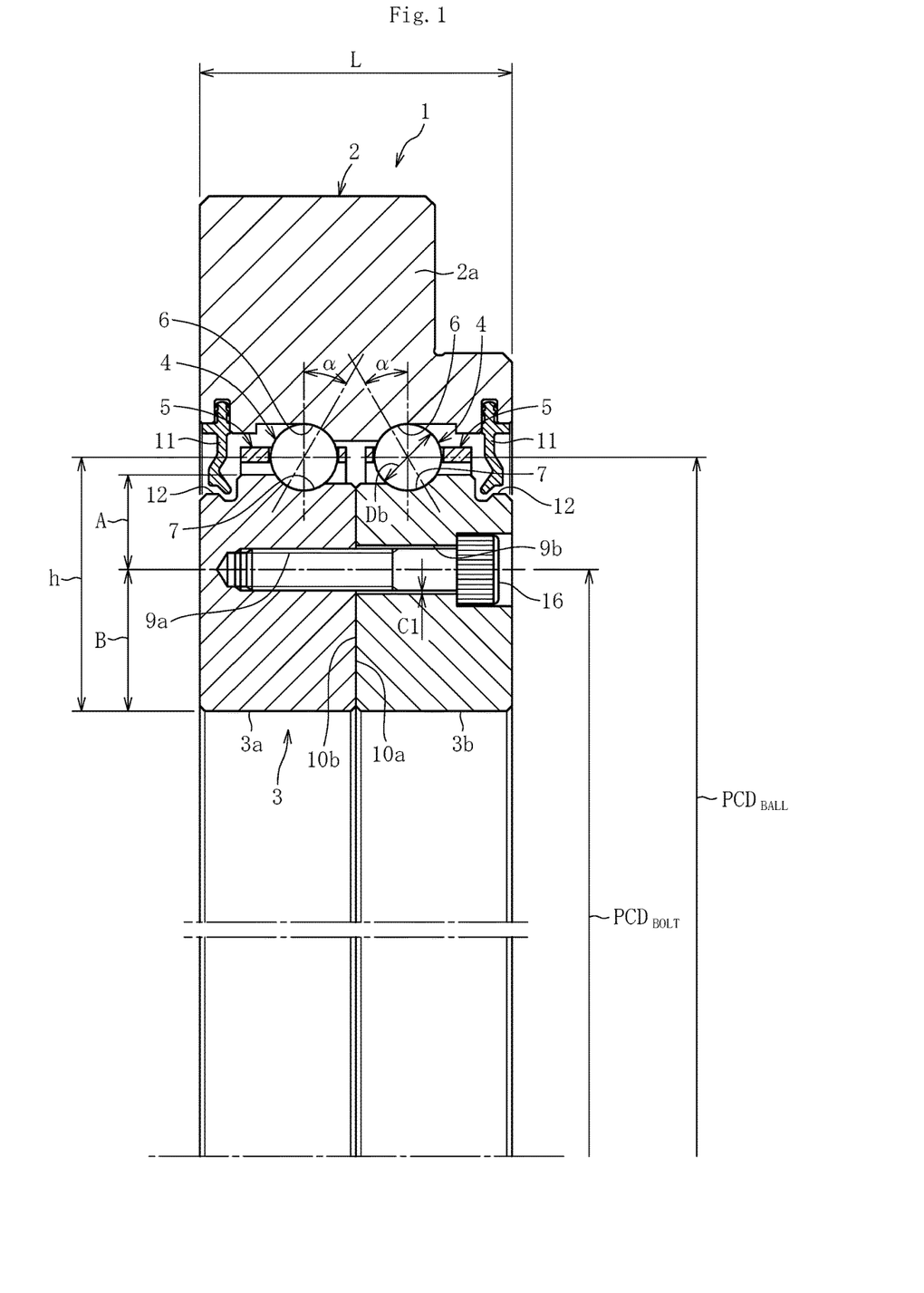
FIG. 1 is a longitudinal sectional view of a double-row angular contact ball bearing for a CT scanning device according to a first embodiment of the present invention.
Figure 2:
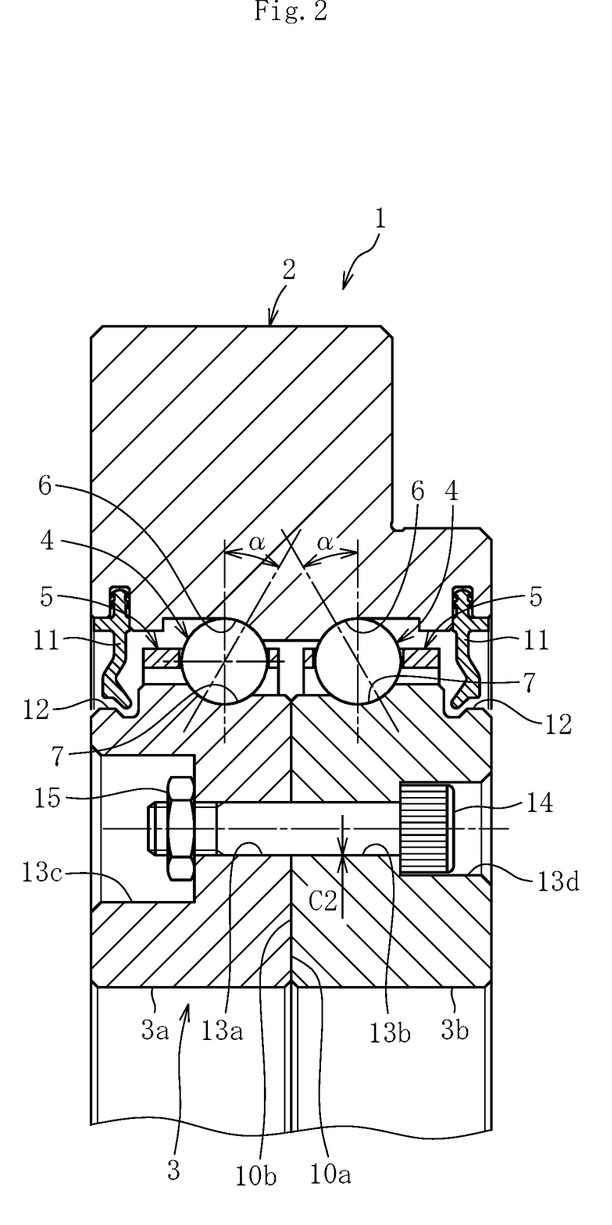
FIG. 2 is a longitudinal sectional view taken at a position different from that of FIG. 1 in a circumferential direction.
Figure 3:
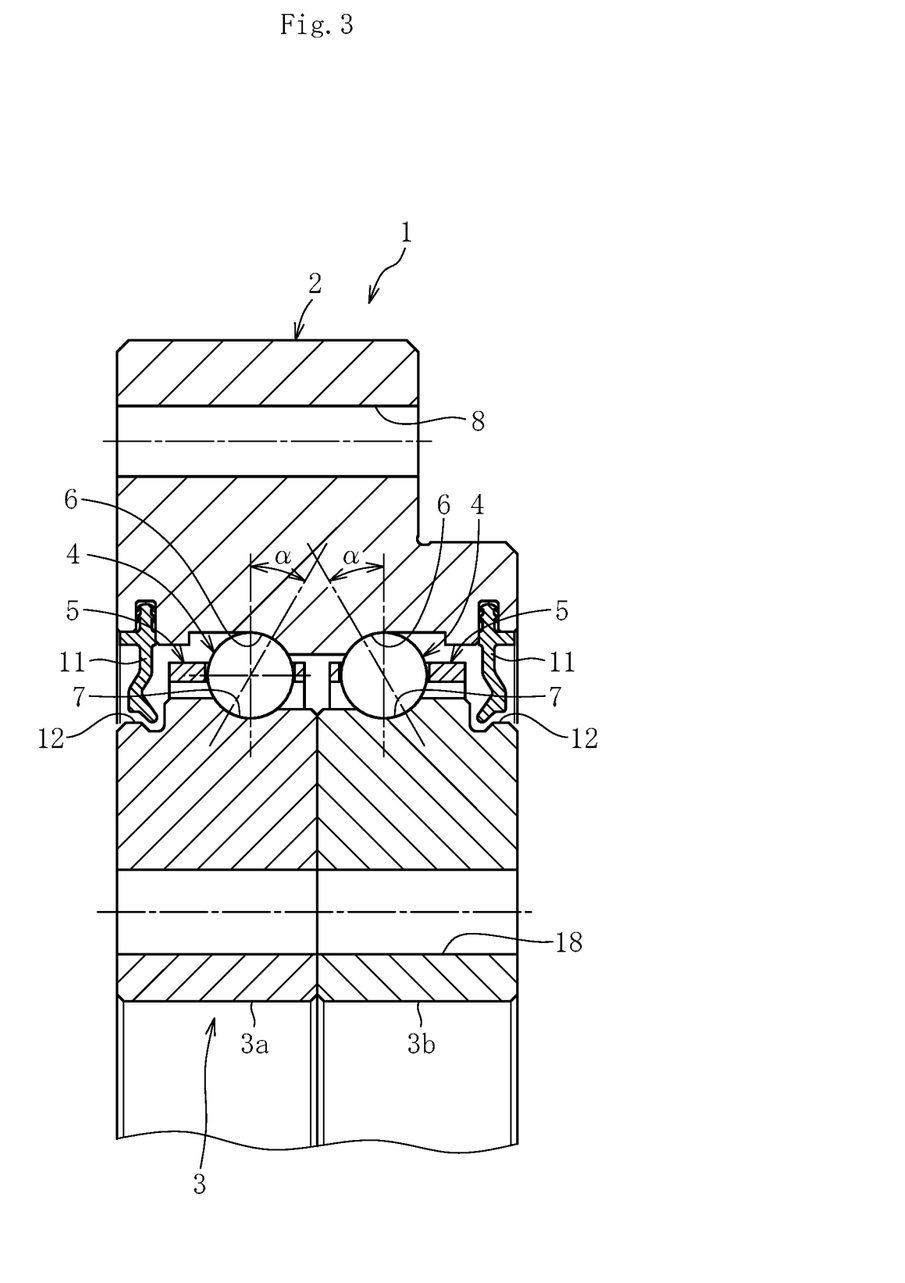
FIG. 3 is a longitudinal sectional view taken at a position different from those of FIG. 1 and FIG. 2 in the circumferential direction.
Figure 5:
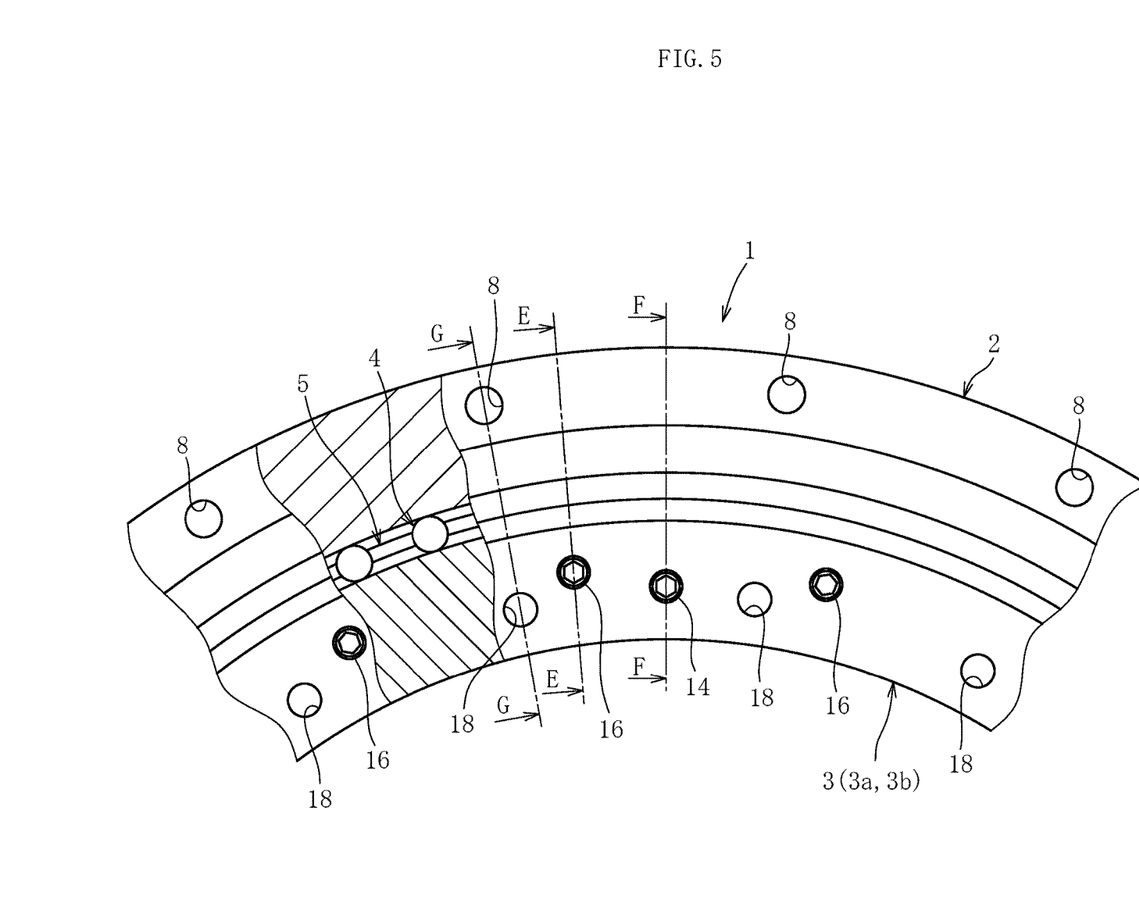
FIG. 5 is a right side view of the double-row angular contact ball bearing for a CT scanning device of FIG. 1.

FIG. 1 to FIG. 3 are longitudinal sectional views of the double-row angular contact ball bearing for a CT scanning device of this embodiment, and FIG. 5 is a partial right side view containing a part of a horizontal cross section. In FIG. 1 to FIG. 3, circumferential positions at which a cross section is taken differ from each other. FIG. 1 is a view for illustrating a longitudinal cross section taken along the line E-E of FIG. 5. FIG. 2 is a view for illustrating a longitudinal cross section taken along the line F-F of FIG. 5. FIG. 3 is a view for illustrating a longitudinal cross section taken along the line G-G of FIG. 5. First, an overall configuration of the double-row angular contact ball bearing for a CT scanning device (hereinafter also referred to simply as "double-row angular contact ball bearing") of this embodiment is described, and then a characteristic configuration thereof is described.

First, with reference to FIG. 5, a schema of a double-row angular contact ball bearing 1 of this embodiment is described. The double-row angular contact ball bearing 1 comprises an outer member 2, an inner member 3, balls 4 as rolling elements, and retainers 5, as a main configuration. The inner member 3 is made up of a pair of raceway rings 3a and 3b, and is fastened and fixed by a fixing bolt 16 on the line E-E of FIG. 5. A plurality of fastening portions by the fixing bolts 16 are provided at appropriate intervals in the circumferential direction.

A reamer bolt 14 is inserted into the inner member 3 to be positioned on the line F-F, which is a circumferential position different from the line E-E of FIG. 5. Mounting holes 8 and 18 are formed on the line G-G, which is another different circumferential position. A plurality of the mounting holes 8 and 18 are formed at appropriate intervals in the circumferential direction. The double-row angular contact ball bearing 1 of this embodiment is a ultrathin type double-row angular contact ball bearing having a ratio $Db/PCD_{BALL}$ of a diameter Db of each of the balls 4 to a pitch circle diameter $PCD_{BALL}$ (see FIG. 1) set to 0.03 or smaller, in which a plurality of, that is, about 110 to 140 balls 4 for one row are incorporated.

Next, a longitudinal cross section of the double-row angular contact ball bearing 1 of this embodiment is described. As illustrated in FIG. 1, the outer member 2 and the inner member 3 are both ring-shaped and arranged concentrically. The inner member 3 is formed of the pair of raceway rings 3a and 3b, and end surfaces 10a and 10b abutting against each other of the raceway rings 3a and 3b have flat surfaces instead of a spigot structure. Two rows of raceway surfaces 6 and 6 are formed on an inner periphery of the outer member 2, and raceway surfaces 7 and 7 opposed to the raceway surfaces 6 and 6 of the outer member 2 are formed on respective outer peripheries of the pair of raceway rings 3a and 3b forming the inner member 3. Two rows of the balls 4 are incorporated into a space between each of the raceway surfaces 6 and 6 of the outer member 2 and each of the raceway surfaces 7 and 7 of the inner member 3. The retainers 5 are arranged between the outer member 2 and the inner member 3, and the balls 4 in each row are held at predetermined intervals in the circumferential direction.

In the double-row angular contact ball bearing 1 of this embodiment, the balls 4 are arranged in two rows, and the bearing portions in both the rows are constructed in back-to-back arrangement. An intersection of action lines of the loads of the rolling elements is positioned on a radially outer side of a pitch circle connecting centers of the balls 4. The balls 4 are held in contact with the raceway surfaces 6 and 7, respectively, at a contact angle $\alpha$, and the contact angle $\alpha$ is set to, for example, about 30°. The inner member 3 is formed of the pair of raceway rings 3a and 3b, and thus the double-row angular contact ball bearing 1 is constructed in back-to-back arrangement, which is advantageous to a moment load. The end surfaces 10a and 10b of the pair of raceway rings 3a and 3b are brought into abutment against each other, thereby being capable of easily setting a bearing clearance (preload or minute clearance). Through the back-to-back arrangement of the double-row angular contact ball bearing 1, a distance between the working points is increased to provide higher stiffness, which is advantageous against the moment load.

A stepped portion 12 is formed on each of the raceway rings 3a and 3b by setting the outer periphery on the axial outer side of each of the raceway rings 3a and 3b to a small diameter. The stepped portion 12 forms a labyrinth in cooperation with a radially inner end portion of a seal member 11 mounted on the inner periphery of the outer member 2. Outer diameters of the respective stepped portions 12 are equal to each other, thereby allowing the use of the common seal member 11 on both sides.

With reference to FIG. 2 that is a longitudinal sectional view taken along the line F-F of FIG. 5, a configuration for suppressing decentering of the pair of raceway rings 3a and 3b is described. As described above, the end surface 10a of the raceway ring 3a and the end surface 10b of the raceway ring 3b, which are held in abutment against each other, are formed as flat surfaces. Reamer holes 13a and 14b as positioning holes are formed in form of through holes in the raceway rings 3a and 3b so as to insert the reamer bolt 14 as a positioning member therethrough. A counter bored portion 13c is formed on an outer side of the positioning hole 13a, whereas a counter bored portion 13d is formed on an outer side of the positioning hole 13b. In this embodiment, the reamer holes 13a and 13b are formed equiangularly at three positions. Although at least two fitting portions between the reamer holes 13a and 13b and the reamer bolt 14 are sufficient to determine a position in a vertical direction and a rotating direction, further stable positioning can be achieved with three fitting portions.

The reamer bolt 14 comprises a radially outer portion finished with high accuracy and is capable of regulating a clearance between the reamer bolt 14 and the reamer holes 13a and 13b of the raceway rings 3a and 3b at a time of fitting. The fitting in this case is required to satisfy a relationship of clearance C1>clearance C2, where C1 represents a clearance between a radially outer part of a fixing bolt 16 (see FIG. 1) and a radially inner part of a fit-insertion hole 9b, and C2 represents a clearance between a radially outer part of the reamer bolt 14 illustrated in FIG. 2 and a radially inner part of the reamer holes 13a and 13b. It is ideal that the reamer bolt 14 and the reamer holes 13a and 13b be actually fitted (fitted in actual assembly operation), if possible. Through use of the reamer bolts 14 as the positioning members, good workability in positioning is provided. A commercial item can be appropriately adopted, which is preferred in terms of quality and cost.

As a method of assembling the double-row angular contact ball bearing 1, the retainers 5 are arranged in two rows inside the raceway surfaces 6 and 6 of the outer member 2. After incorporating the balls 4 and 4 in pockets of the retainers 5, the pair of raceway rings 3a and 3b forming the inner member 3 are inserted to a radially inner side of the balls 4 and 4 so as to be pressed in a direction in which the end surface 10a of the raceway ring 3a and the end surface 10b of the raceway ring 3b are brought into abutment against each other. Then, the seal members 11 and 11 are mounted in seal mounting grooves formed on both axial ends of a radially inner surface of the outer member 2, and grease as a lubricating oil is enclosed inside.

Figure 4:
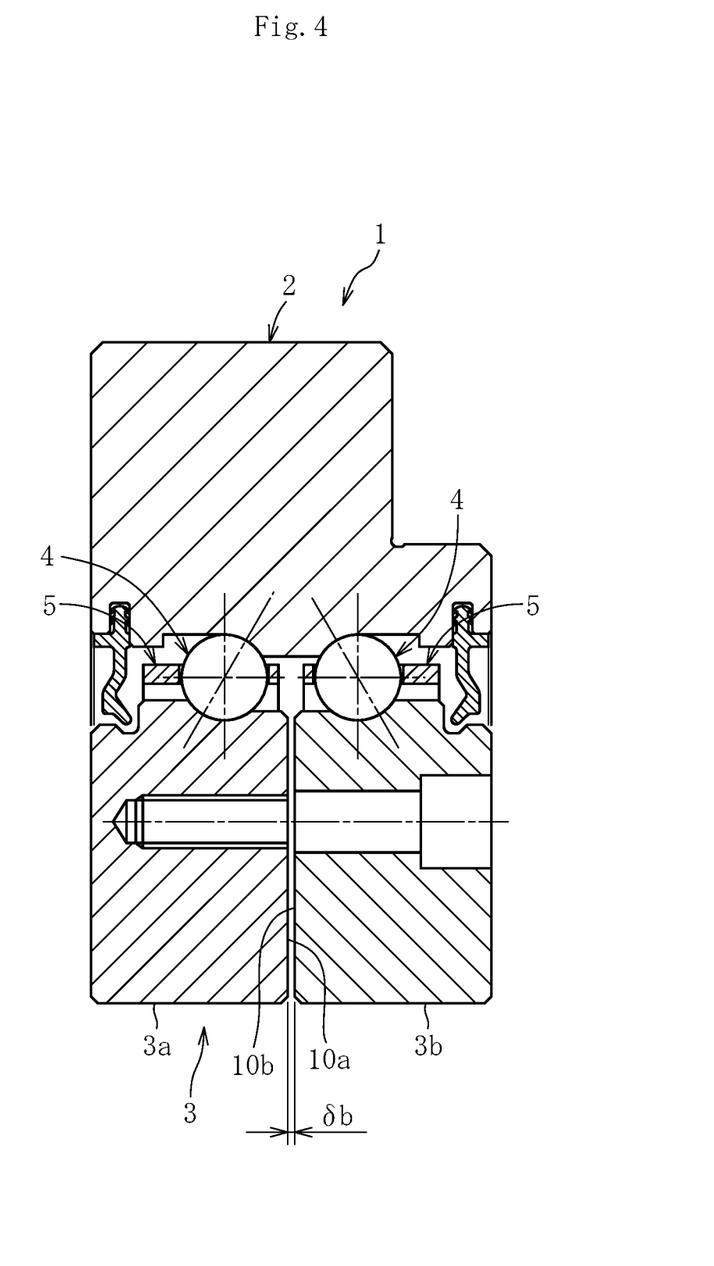
FIG. 4 is a longitudinal sectional view of an axial clearance before assembly of the double-row angular contact ball bearing for a CT scanning device of FIG. 1.

A state in which the pair of raceway rings 3a and 3b is incorporated so that the balls 4 and both the raceway surfaces 6 and 7 are held in abutment against each other is illustrated in FIG. 4. In this state, a set axial clearance δb is set between the end surfaces 10a and 10b of the pair of raceway rings 3a and 3b. It is desired that the set axial clearance δb be set to satisfy at least δa<δb for an axial maximum deformation amount δa of the raceway rings 3a and 3b when the moment load is applied.

Thereafter, the reamer bolt 14 is inserted into the reamer holes 13a and 13b respectively formed in the pair of raceway rings 3a and 3b. A nut 15 is threadably mounted on the reamer bolt 14 so as to be temporarily fixed. In this manner, positioning is achieved in a state in which the pair of raceway rings 3a and 3b is centered. In this state, the set axial clearance δb still remains.

In a state in which the raceway rings 3a and 3b are positioned by the reamer bolt 14 and the nut 15, the fixing bolt 16 is inserted into the fit-insertion hole 9b so as to be threadably fitted into a screw hole 9a, and is fastened to be fixed until the end surface 10a of the raceway ring 3a and the end surface 10b of the raceway ring 3b come into abutment against each other. The plurality of fixing bolts 16 are provided in the circumferential direction. When the fixing bolts 16 are screwed and fastened until the end surfaces 10a and 10b come into abutment against each other as described above, the above-mentioned set axial clearance δb is eliminated. An appropriate preload (for example, from about −30 μm to about −10 μm) obtained by a preload at a fixed position is uniformly obtained as a bearing clearance for the left and right raceway rings 3a and 3b in two rows. As a result, stable bearing performance with high stiffness can be obtained.

The double-row angular contact ball bearing 1 of this embodiment does not have the spigot structure for the pair of raceway rings 3a and 3b, and is therefore easy to manufacture to achieve a cost reduction.

As illustrated in FIG. 3 that is a longitudinal sectional view taken along the line G-G of FIG. 5, the mounting holes 8 and 18 are formed. The mounting hole 8 formed in the outer member 2 is fastened and fixed to, for example, a fixing portion 106 of a CT scanning device 100 illustrated in FIG. 9 by a bolt (not shown). The mounting hole 18 formed in the inner member 3 is fastened and fixed to a rotator 105 by a bolt (not shown). A plurality of the mounting holes 8 and 18 are formed in the circumferential direction.

In a normal state of use in which the inner diameter and the outer diameter of the bearing are fitted to a shaft or a housing, radial decentering is restricted by fitting the pair of raceway rings forming the inner member to the shaft. However, the double-row angular contact ball bearing 1 for a CT scanning device is fastened and fixed to a target member of a used device on a bearing width surface by a bolt. Therefore, the raceway rings 3a and 3b in two rows are relatively shifted in the radial direction. When the moment load is exerted, in particular, the effects thereof are great. Therefore, there is a fear of a problem such as a preload loss in this state of use. Although the state of use is severe as described above, further increase in speed and further quietness are required in the future so as to alleviate anxiety of patients and prevent atrophy of internal organs.

The overall configuration of the double-row angular contact ball bearing 1 for a CT scanning device of this embodiment has been described. Next, a characteristic configuration is described. A characteristic configuration of the double-row angular contact ball bearing 1 of this embodiment resides in that, based on a structure in which the decentering of the pair of raceway rings is suppressed by the positioning members inserted into the positioning holes, a dimensional relationship between the diameter Db of each of the balls and the radial dimension h from the center of the ball to the inner diameter of the inner member is set as a first parameter so as to satisfy Db/h≤0.26. Further, based on the center of the fixing bolt as a reference, a dimensional relationship between a radial thickness A from the center to the outer diameter of the inner member and a radial thickness B from the center to the inner diameter of the inner member is set as a second parameter so as to satisfy B>A.

More specifically, with reference to FIG. 1, in the double-row angular contact ball bearing 1 of this embodiment, a radial thickness of a portion of the outer member 2 except for a mounting flange 2a is reduced at maximum in view of a shear stress, deformation due to thermal processing, and the sealing grooves so as to maximize the pitch circle diameter $PCD_{BALL}$ of each of the balls 4. In this manner, the number of balls 4 can be increased, while the radial thickness of the inner member 3 is maximized, thereby increasing a load capacity and the stiffness.

A ratio of the diameter Db of each of the balls 4 to the radial dimension h from the center of the ball 4 to the inner diameter of the inner member 3 is Db/h=0.26, specifically, is set to satisfy Db/h≤0.26. A pitch circle obtained by connecting the centers of the balls 4 has the pitch circle diameter $PCD_{BALL}$.

Further, the radial dimension A from the center of each of the fixing bolts 16 to the outer diameter of the inner member 3 and the radial dimension B from the center of each of the fixing bolts 16 to the inner diameter of the inner member 3 are set to satisfy B/A=1.57, specifically, are set to satisfy B>A. A pitch circle obtained by connecting the centers of the fixing bolts 16 has a pitch circle diameter $PCD_{BOLT}$. The fit-insertion hole 9b and the screw hole 9a for the fixing bolt 16 are formed as close as possible to a radially outer side in consideration of a necessary thickness to the outer diameter of the raceway rings 3a and 3b so as to be advantageous against the moment load. Therefore, the radial dimension A from the center of each of the fixing bolts 16 to the outer diameter of the inner member 3 is approximately constant, and is increased so as to correspond to an increase in dimension of the pitch circle diameter $PCD_{BALL}$ of each of the balls 4. As a result, the radial dimension B from the center of each of the fixing bolts 16 to the inner diameter of the inner member 3 can be increased.

The double-row angular contact ball bearing 1 of this embodiment is set to have the above-mentioned dimensional relationships, and therefore can realize a further increase in speed and further quietness in the future.

Further, a ratio of the diameter Db of each of the balls 4 and a total bearing width L is set to satisfy Db/L≥0.21. In this manner, a space reduction can be achieved.

Next, various examinations, verifications, and findings until achievement of this embodiment are supplementarily described.

[Examinations on Double-Row Angular Contact Ball Bearing for CT Scanning Device in Terms of Structure]

In the double-row angular contact ball bearing for a CT scanning device, which has a structure in which the decentering of the pair of raceway rings is suppressed by the positioning members inserted into the positioning holes, the pair of raceway rings is fastened with the plurality of fixing bolts in a state in which the pair of raceway rings is centered by using the necessary minimum number of (for example, three) positioning members. It is proven that the double-row angular contact ball bearing having the precondition structure is sensitive to abnormal noise in a higher speed rotation region. The reason is considered to be an effect of the fastening structure only with the fixing bolts without the spigot structure between the pair of raceway rings.

[Bearing Mounting Space]

A mounting space for a bearing to be used is determined for each kind of CT scanning device, and therefore has a restriction that an outer-diameter dimension, an inner-diameter dimension, and a width dimension of the bearing cannot be changed. Further, a diameter of the ball as the rolling element to be incorporated into the bearing is approximately constant. As a result of various thinkings in consideration of the above-mentioned restrictions, attention is focused on a possibility of increasing the thickness of the pair of raceway rings constructing the inner member by increasing the pitch circle diameter $PCD_{BALL}$ of the ball.

[Verification of Limit rpm at Which Acoustic Property is Good]

Under a condition where the bearing mounting space is constant, the double-row angular contact ball bearings, which each have the precondition structure with various pitch circle diameters $PCD_{BALL}$ of the ball and raceway ring thicknesses, were manufactured so as to measure a limit rpm at which an acoustic property is good (no abnormal noise is generated). As a result, it was proven that there was a difference in limit rpm at which no abnormal noise was generated even when the bearing mounting space was the same.

Figure 7:
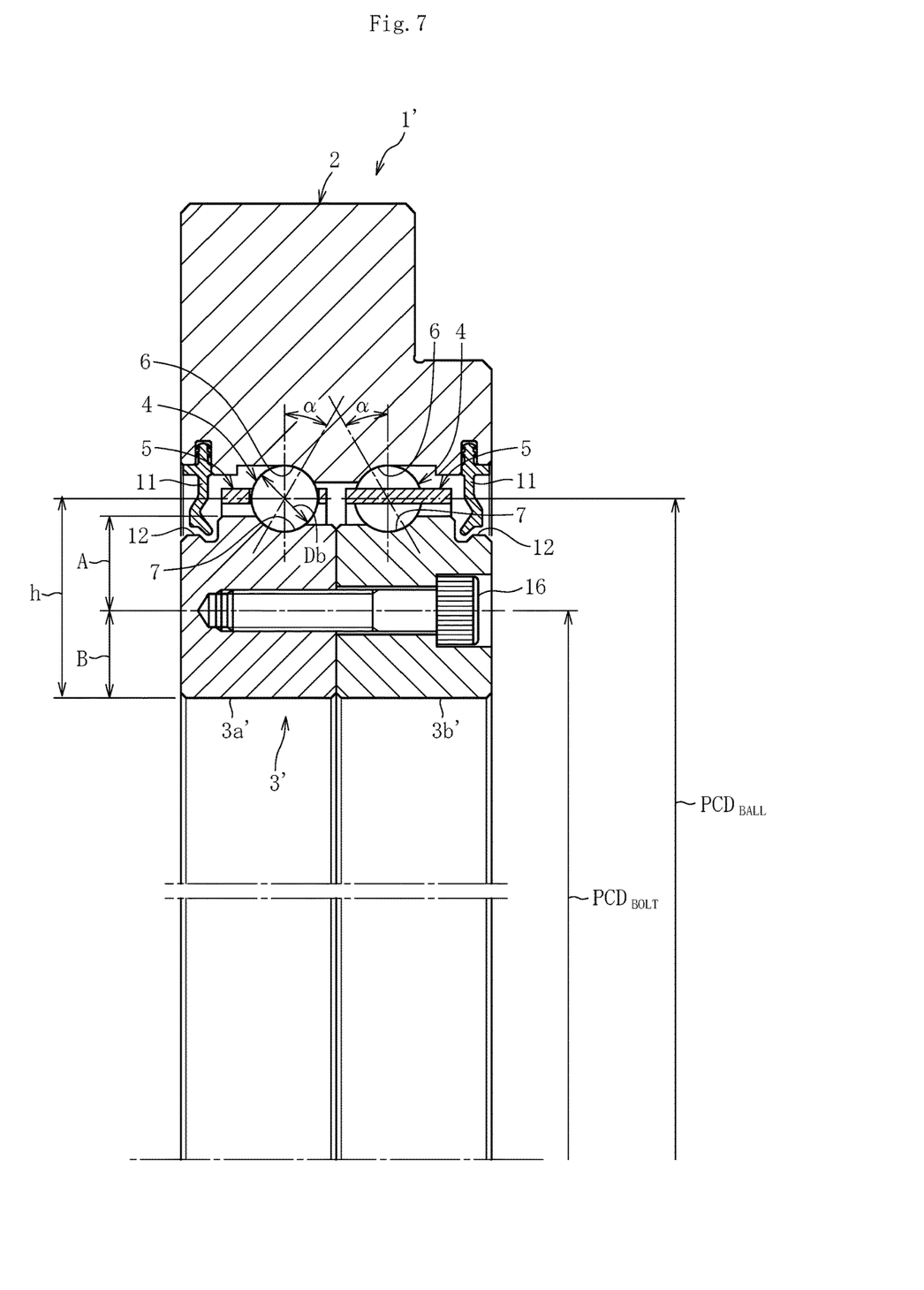
FIG. 7 is a longitudinal sectional view of the double-row angular contact ball bearing for a CT scanning device for illustrating findings obtained in a development process.

The contents of the verification described above are specifically described. In FIG. 7, an example of a double-row angular contact ball bearing manufactured in a development process is illustrated. FIG. 7 corresponds to a longitudinal sectional view taken along the line E-E of FIG. 5. In a double-row angular contact ball bearing 1', a ratio Db/h of the diameter Db of each of the balls 4 to the radial dimension h from the center of each of the balls 4 to an inner diameter of an inner member 3' is 0.31. Further, the radial dimension A from the center of each of the fixing bolts 16 to an outer diameter of the inner member 3' and the radial dimension B from the center of each of the fixing bolts 16 to the inner diameter of the inner member 3' are approximately equal, and therefore satisfy A≈B. Besides the dimensional relationships, various samples were manufactured.

Figure 6:
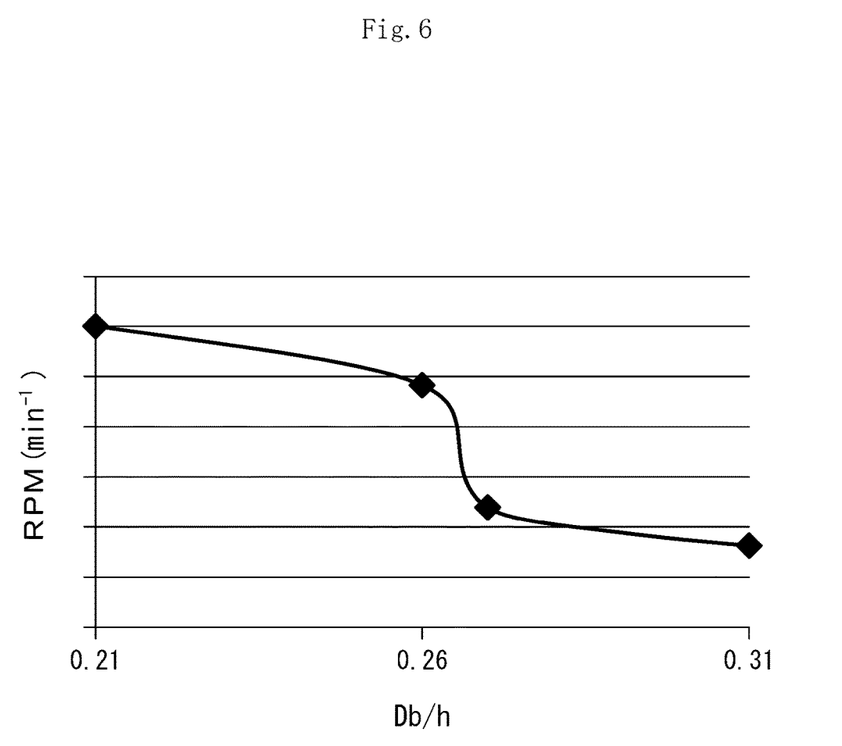
FIG. 6 is a graph for showing a result of measurement of a limit rpm.

For the samples having the various dimensional relationships, a limit rpm at which the acoustic property was good without generation of abnormal noise was measured. A result of measurement is shown in FIG. 6. As a result, it was verified that the double-row angular contact ball bearing for a CT scanning device, which had the structure in which the decentering of the pair of raceway rings was suppressed by the positioning members inserted into the positioning holes, was sensitive to abnormal noise in a higher speed rotation region (for example, 200 min$^{-1}$ or higher). Further, it was proven that there was a difference in limit rpm at which the abnormal noise was not generated even with the same bearing mounting space.

From the result of measurement, it was proven that the limit rpm was dramatically improved at Db/h of 0.26 as shown in FIG. 6. This remarkable tendency of the limit rpm is considered because of an extremely large number of balls incorporated in the double-row angular contact ball bearing 1 for a CT scanning device as described above and of properties of the abnormal noise generated due to an extremely small behavior in a portion where the preload loss is generated when the balls roll at a high speed. Further, a dimensional relationship between A and B exhibiting the same tendency as that of the parameter was found. This is considered because, as described above, the radial dimension A from the center of each of the fixing bolts 16 to the outer diameter of the inner member 3 increases correspondingly to an increase in pitch circle diameter $PCD_{BALL}$ of each of the balls 4.

[Idea of New Parameters]

The results of verifications described above were analyzed to find the following two new parameters as indices of the double-row angular contact ball bearing having the precondition structure capable of achieving a further increase in speed.

[First Parameter]: A dimensional relationship between the diameter Db of each of the balls and the radial dimension h from the center of each of the balls to the inner diameter of the inner member.

[Second Parameter]: A dimensional relationship between the radial dimension A from the center of each of the fixing bolts to the outer diameter of the inner member and the radial dimension B from the center of each of the fixing bolts to the inner diameter of the inner member, based on the center of the fixing bolt as a reference.

Then, through settings of Db/h≤0.26 as the first parameter and B>A as the second parameter, the limit rpm at which the abnormal noise was not generated was dramatically improved to achieve this embodiment. The reason why the limit rpm at which the abnormal noise is not generated is improved is considered because the stiffness of the inner member 3 is increased so that the preload loss in a portion in which a rolling element load is small is successfully prevented when the moment load is exerted.

Figure 8:
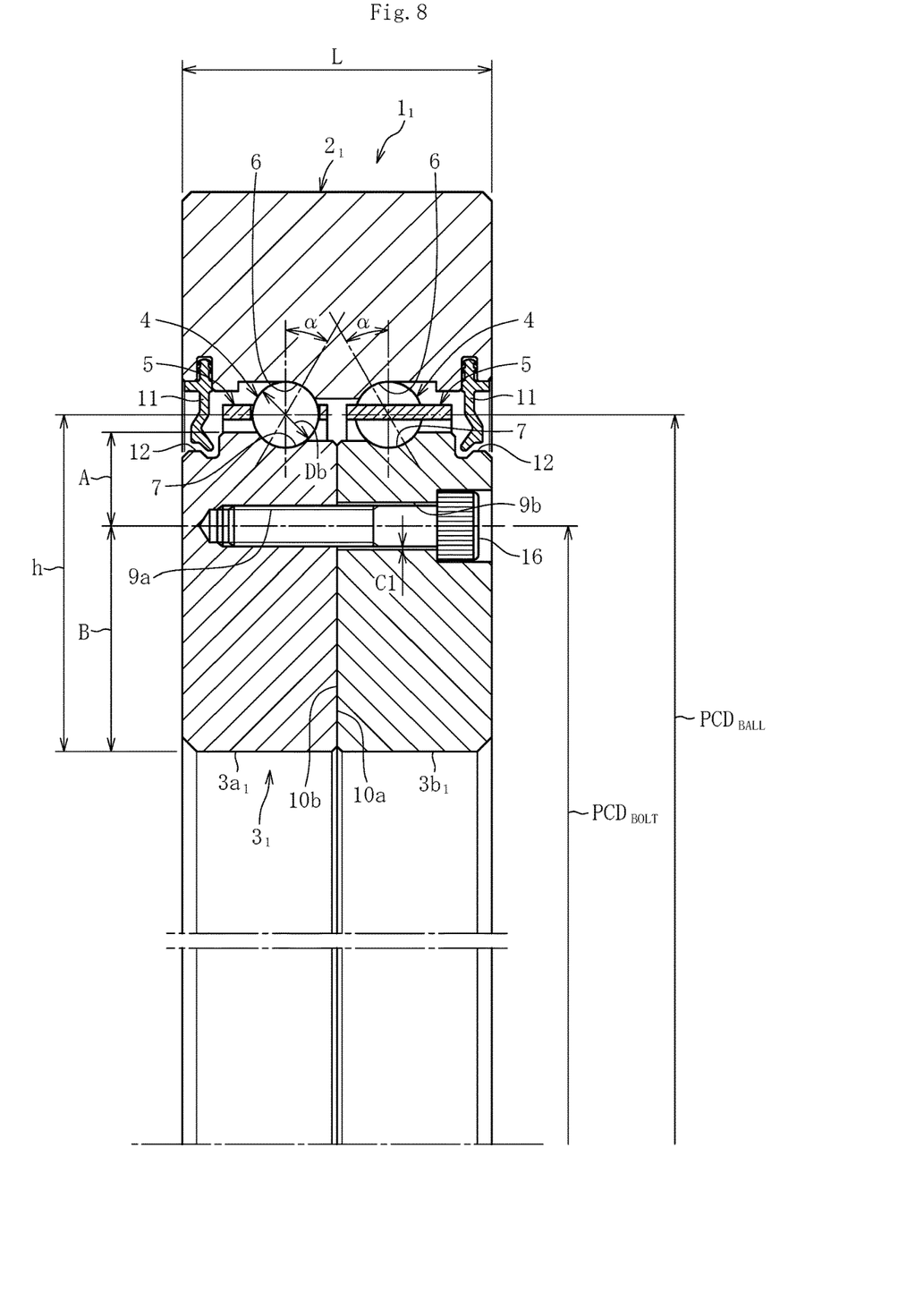
FIG. 8 is a longitudinal sectional view of a double-row angular contact ball bearing for a CT scanning device according to a second embodiment of the present invention.

Next, a second embodiment of the present invention is described with reference to FIG. 8. In a double-row angular contact ball bearing of this embodiment, a mounting hole (not shown) passing through the outer member in the axial direction is formed without providing the mounting flange to the outer member. FIG. 8 corresponds to a longitudinal cross section taken along the line E-E of FIG. 5 according to the first embodiment. The longitudinal cross sections of the first embodiment, taken along the line F-F and the line G-G of FIG. 5, are functionally similar. Parts having similar functions are denoted by the same reference symbols (except for a subscript), and the description of the configuration and the functions and effects in the first embodiment are used therefor. Now, differences from the first embodiment are described.

In a double-row angular contact ball bearing $1_1$ of this embodiment, the pitch circle diameter $PCD_{BALL}$ of each of the balls 4 is set to a further increased diameter as compared to that of the first embodiment. In this manner, the number of balls 4 can be further increased, while a radial thickness of an inner member $3_1$ can be further increased, thereby further increasing the load capacity and the stiffness.

In this embodiment, the ratio of the diameter Db of each of the balls 4 to the radial dimension h from the center of each of the balls 4 to the inner diameter of the inner member $3_1$ is Db/h=0.21, specifically, is set to satisfy Db/h≤0.26.

Further, a relationship between the radial dimension A from the center of each of the fixing bolts 16 to an outer diameter of the inner member $3_1$ and the radial dimension B from the center of each of the fixing bolts 16 to the inner diameter of the inner member $3_1$ is B/A=2.29, specifically, is set to satisfy B>A.

The double-row angular contact ball bearing $1_1$ of this embodiment is set to have the above-mentioned dimensional relationships, and therefore is capable of realizing a further increase in speed and further quietness in the future.

Further, the ratio of the diameter Db of each of the balls 4 to the total bearing width L is set to satisfy Db/L≥0.21. In this manner, the space reduction can be achieved.

In the embodiments described above, the reamer bolts have been exemplified as the positioning members. However, the positioning members are not limited thereto, and may also be positioning pins. When the positioning pin and the reamer hole are fitted through appropriate interference fit, a fixing part for the positioning pin is not required. Further, a commercial item can be appropriately adopted as the positioning pin. Thus, the positioning pin is preferred in terms of quality and cost.

The present invention is not limited to the above-mentioned embodiments. As a matter of course, the present invention may be carried out in various other embodiments without departing from the gist of the present invention. The scope of the present invention is defined by the claims, and encompasses meanings of equivalents of elements described in the claims and all modifications within the scope of the claims.

DESCRIPTION OF REFERENCE SIGNS 1 double-row angular contact ball bearing for CT scanning device
2 outer member
3 inner member
3a raceway ring
3b raceway ring
4 rolling element
5 retainer
6 raceway surface
7 raceway surface
8 mounting hole
9a screw hole
9b fit-insertion hole
10a end surface
10b end surface
13a positioning hole
13b positioning hole
14 reamer bolt
16 fixing bolt
18 mounting hole
100 CT scanning device
A radial thickness
B radial thickness
Db diameter of ball
h radial dimension
L total bearing width
$PCD_{BALL}$ pitch circle diameter of ball
$PCD_{BOLT}$ pitch circle diameter of fixing bolt
α contact angle
δb set axial clearance

The invention claimed is:

1. An ultra-thin double-row angular contact ball bearing for a CT scanning device, the ultra-thin double-row angular contact ball bearing comprising:
   an outer member having raceway surfaces in two rows on an inner periphery;
   an inner member having raceway surfaces in two rows on an outer periphery and being arranged on an inner side of the outer member;
   balls in two rows incorporated between the raceway surfaces of the outer member and the raceway surfaces of the inner member; and
   retainers configured to hold the balls,
   the inner member being made up of a pair of raceway rings,
   the pair of raceway rings having at least two pairs of positioning holes into each pair of which a positioning member is inserted, wherein a clearance is defined between each of the pairs of positioning holes and the associated positioning member, the clearance being restricted to suppress radial decentering of the pair of raceway rings,
   the pair of raceway rings being fastened together by a plurality of fixing bolts, wherein the centers of the positioning members are located at a different radial position than the centers of the fixing bolts,
   the inner member having an inner diameter of 650 mm or more, and a value of a ratio $Db/PCD_{BALL}$ being 0.03 or less, where Db represents a diameter of each of the balls and $PCD_{BALL}$ represents a pitch circle diameter of the balls,
   the pair of raceway rings having opposed end surfaces that are formed as flat surfaces and being fastened by the plurality of fixing bolts to bring the opposed end surfaces into abutment against each other to apply a preload at a fixed position between the balls and the raceway surfaces,
   the following relationship being set:

$Db/h≤0.26$, where h represents a radial dimension from a center of each of the balls to the inner diameter of the inner member, and the following relationship being set:

$B>A$, where A represents a radial dimension from the center of each of the plurality of fixing bolts to an outer diameter of the inner member, and B represents a radial dimension from the center of each of the plurality of fixing bolts to the inner diameter of the inner member.

2. The ultra-thin double-row angular contact ball bearing for a CT scanning device according to claim 1, wherein the double-row angular contact ball bearing has a back-to-back arrangement.

3. The ultra-thin double-row angular contact ball bearing for a CT scanning device according to claim 1, wherein a ratio of the diameter of each of the balls to a total bearing width is set to satisfy:

$Db/L≥0.21$ where L represents a total bearing width of the double-row angular contact ball bearing for the CT scanning device.

4. The ultra-thin double-row angular contact ball bearing for a CT scanning device according to claim 1, wherein the positioning member comprises a reamer bolt.

5. The ultra-thin double-row angular contact ball bearing for a CT scanning device according to claim 1, wherein the positioning holes of the pair of raceway rings have diameters that are constant through the raceway rings.

6. The ultra-thin double-row angular contact ball bearing for a CT scanning device according to claim 5, wherein the diameters of the positioning holes of the raceway rings are the same.

7. The ultra-thin double-row angular contact ball bearing for a CT scanning device according to claim 1, wherein a full length of inner surfaces of the positioning holes of the pair of raceway rings are smooth.

8. The ultra-thin double-row angular contact ball bearing for a CT scanning device according to claim 1, wherein the positioning holes of the pair of raceway rings have straight cylindrical inner surfaces.

\* \* \* \* \*